US010149826B2

(12) United States Patent
Jain

(10) Patent No.: US 10,149,826 B2
(45) Date of Patent: Dec. 11, 2018

(54) METHOD OF PREPARING MICROSPHERES

(71) Applicant: Hyalo Technologies, LLC, Mendham, NJ (US)

(72) Inventor: Shalabh Jain, Mendham, NJ (US)

(73) Assignee: HYALO TECHNOLOGIES, LLC, Philadelphia, PA (US)

( * ) Notice: Subject to any disclaimer, the term of this patent is extended or adjusted under 35 U.S.C. 154(b) by 282 days.

(21) Appl. No.: 14/600,735

(22) Filed: Jan. 20, 2015

(65) Prior Publication Data

US 2016/0206563 A1 Jul. 21, 2016

(51) Int. Cl.
*A61K 9/00* (2006.01)
*A61K 9/16* (2006.01)

(52) U.S. Cl.
CPC .......... *A61K 9/1694* (2013.01); *A61K 9/1647* (2013.01); *A61K 9/1652* (2013.01)

(58) Field of Classification Search
None
See application file for complete search history.

(56) References Cited

U.S. PATENT DOCUMENTS

| | | | | |
|---|---|---|---|---|
| 3,204,934 | A | 9/1965 | Graham et al. | |
| 3,463,842 | A * | 8/1969 | Flack | B01J 2/08 252/635 |
| 6,669,961 | B2 | 12/2003 | Kim et al. | |
| 2003/0230819 | A1 | 12/2003 | Park et al. | |
| 2006/0071357 | A1 | 4/2006 | Pilon et al. | |
| 2007/0264341 | A1 | 11/2007 | Lee et al. | |

FOREIGN PATENT DOCUMENTS

| | | | | |
|---|---|---|---|---|
| WO | 9528227 | A1 | 10/1995 | |
| WO | WO-9717933 | A1 * | 5/1997 | A61H 23/0245 |

OTHER PUBLICATIONS

Felder et al (Ultrasonic atomization and subsequent polymer desolvation for peptide and protein microencapsulation into biodegradable polyesters, Journal of Microencapsulation, 20:5, 553-567, 2003).*
Berkland et al (Fabrication of PLG microspheres with precisely controlled and monodisperse size distributions, Journal of Controlled Release 73 (2001) 59-74).*
James M. Anderson, et al., Biodegradation and Biocompatibility of PLA . . . , Advanced Drug Delivery Reviews, vol. 64, pp. 72-82, 2012.
V.R. Sinha, Aman Trehan, Biodegradable Microspheres for Protein Delivery, Journal of Controlled Release, vol. 90, pp. 261-280, 2003.
Lian-Yan Wang, et al., Preparation of Uniform Sized Chitosan Microspheres by Membrane . . . , Journal of Controlled Release, vol. 106, pp. 62-75, 2005.
Lawrence K. Fung, et al., Polymeric Implants for Cancer Chemotherapy, Advanced Drug Delivery Reviews, vol. 26, pp. 209-230, 1997.
European communication corresponding to EP16740582.8 dated Jul. 4, 2018.

* cited by examiner

*Primary Examiner* — Robert S Loewe
*Assistant Examiner* — Rachel Kahn
(74) *Attorney, Agent, or Firm* — Lucas & Mercanti, LLP

(57) ABSTRACT

Methods of preparing particles using a sonication device are disclosed. The methods include directing a particle forming solution containing a particle forming liquid and a particle forming agent as a stream into contact with a sonicating tip of a sonication device under conditions sufficient to transform the stream containing the particle forming solution into a plurality of droplets having a substantially uniform size. The plurality of droplets are contacted with a hardening solution under conditions sufficient to solidify the droplets into particles having a substantially uniform particle size which are then recovered. Particles made in accordance with the methods can be solid or semi-solid and range in size from sub-micron to over 100 microns in diameter.

33 Claims, 4 Drawing Sheets

METHOD OF PREPARING MICROSPHERES

BACKGROUND OF INVENTION

Polymer particles of size in the range of few nanometers to several hundred micrometers have been of interest as delivery vehicles for pharmaceutical and biotechnology products. Several products based on this technology have been approved by the USFDA for use in humans. The particles are known by several names including microparticles, microspheres and nanoparticles. These particles can contain dissolved or dispersed active drug molecules for prolonged delivery to the body. Typically, the drug is dispersed in the particles during their formation. The drug-polymer matrix in the form of particles can be injected at various locations in the body. The particles are typically prepared from biodegradable polymers. As the particles slowly dissolve, they release the active medicament for absorption into the body. This can allow for active levels of the medicament in the body for as long as 3 months following a single injection.

The particles can also be used without an active ingredient incorporated in them. In such a case, the particles act as a medical device. Examples of such devices can cause arterial embolism to kill cells, a tissue, etc. or elicit an immune reaction from the body.

Microspheres have can be prepared by a variety of methods. These methods rely on the use of techniques such as precipitation or co-precipitation, forming an emulsion by rapid stirring or sonication in mutually immiscible liquids. Some other methods also use a nozzle spray to atomize the particle forming agent in a solution form in a suitable solvent. In all of the methods involving a particle forming agent dissolved in the particle forming solvent, the droplets of the particle forming solution are added to another solution called as the hardening solution. The hardening solution contains ingredients such as surfactants or chemical reactants that cause the particles to harden either by loss of solvent or by a chemical reaction resulting in formation of a new material.

In the methods involving bulk sonication, the polymer forming the particle is dissolved in a suitable first solvent and this solution is added to the second solvent in which the first solvent is not soluble. This is followed by either bath sonication or tip sonication that results in a fine dispersion of the polymer solution. In this method, either a sonication tip is dipped in the solutions or the solutions are added to a sonication bath This method has the drawback of applying sonication energy to the entire system repeatedly, resulting the formation of small microspheres in the range of less than one micron to about 20 microns. However, this method also results in the formation of microspheres of highly variable particle sizes which is not desirable.

In the spray based methods, the polymer solution is typically sprayed as a fine mist in to a chamber where the particles may dry very quickly (spray drying) or the droplets may drop in a second solvent and be stirred until the first solvent evaporates, leaving behind the solid particles. This method involves application of pressure to force the polymer solution through the nozzle and once again results in a large particle size distribution as indicated by a high relative standard deviation in the size of the microparticles. Yet another disadvantage of this method is that it cannot produce particles of larger than about 50 micrometers in diameter.

In one variation of the nozzle spray method, the polymer solution is pumped through a small orifice. The orifice is simultaneously subjected to shaking using an acoustic type wave. This method dislodges the droplets from the nozzle at a regular rate that depends on the frequency of the acoustic wave, thereby resulting in the formation of a single droplet at a time. This allows for a tight control of the droplet size, and results in the formation of particles with a very tight size distribution. This method, however, suffers from several disadvantages. This method involves application of high pressure for pumping the solution through the orifice. This limits the rate at which the solution can be pumped and becomes difficult to sustain when viscosity values of the polymer solution increase beyond a certain limit. Therefore, this method is generally applicable to relatively dilute polymer solutions at a small flow rates. Another disadvantage of this method is that it relies on the formation of one droplet at a time, thereby limiting the scalability of the process. Yet another disadvantage of this method is that it cannot produce particles with size higher than 100 microns. See, for example, U.S. Pat. No. 6,669,961.

Additional methods of preparing microparticles include the use of homogenizers or intensive stirring in order to disperse the polymer solution in a hardening solution. Additionally, the polymer solution may be sprayed from a nozzle or a similar device followed by drying of the particles in air. Several publications have outlined the details of these methods (e.g. Journal of Controlled Release, 90 (2003), pages 261-280; Journal of Controlled Release 106 (2005) pages 62-75). There are at least two disadvantages associated with these methods. First, the particle size range covers mostly smaller sizes, ranging from less than one micron to about 50 microns. Second, none of the methods described previously are easily scalable at a manufacturing scale to produce large amount of particles. The present invention addresses these and other disadvantages.

OBJECTS AND SUMMARY OF INVENTION

A first object of the invention is to produce microparticles as a continuous stream from the flow of solution containing particle forming ingredient or ingredients using a combination of sonication frequency and amplitude.

Another object of the invention to produce microparticles using a sonication method wherein sonication energy is applied to the solution containing the particle forming ingredient or ingredients only once, instead of repeatedly applying the sonication energy to the solution or the droplets.

In accordance with these and other further objects, the present invention provides novel methods to produce microparticles of a pre-selected size range and, if desired, a relatively narrow size distribution. At the same time, the inventive methods allow particles to be formed within a large range of from a few nanometers to several hundred micrometers. In a first aspect thereof, the methods include preparing a plurality of droplets having a substantially uniform particle size by directing a particle forming solution comprising a particle forming liquid and a particle forming agent, as a stream into contact with a sonicating tip of a sonication device under conditions sufficient to transform the stream containing the particle forming solution into a plurality of droplets having a substantially uniform size. In a further aspect of the invention, the plurality of droplets having a substantially uniform size are contacted with a hardening solution under conditions sufficient to solidify the plurality of droplets into a plurality of particles having a substantially uniform particle size.

As will be described in more detail below, the stream of particle forming solution comes in contact with a metal or non-metal tip of the sonication device which breaks up the stream of the particle forming solution into small droplets using sonication energy.

One of the advantages associated with the methods described herein is its scalability. Since the methods use a continuous stream of particle forming solutions which eventually form the desired microspheres, the methods can be scaled up easily to processes in which several hundred grams or kilograms of microparticles can be made in a short period of time. One example of the scalability is to provide a sonication device with multiple tips for the stream to contact and thus further speed up the process.

The methods described herein differ from prior art methods using acoustic technology to form microparticles. In prior art acoustic technology, a single droplet of particle forming solution is produced by forcing the solution through a nozzle and is detached from the nozzle by vibrations produced by the acoustic energy. However, in the methods of the present invention, it is the longitudinal movement of a sonication device that breaks up the flow of a particle forming solution into droplets. In particular, instead of vibrating, the sonication tip or device changes its physical dimensions in the longitudinal plane resulting in a repeated application of force to break the continuous flow of the particle forming solution into droplets within a pre-selected size distribution or with a defined diameter.

It has been found that there are advantages associated with a system where sonication energy is applied to a stream of the particle forming solution only once, resulting in the formation of droplets of a relatively tight size range. Once these droplets leave the tip of the sonication device, they drop into a second solution, described herein as a hardening solution containing a surfactant or a similar stabilizer, that allows the droplets to remain suspended individually until the solvent, which part of the particle forming solution, and therefore part of the droplets falling into the hardening solution, evaporates to yield preferably solid particles.

The stream of the particle forming solution is broken into droplets using the longitudinal expansion and contraction of a sonication probe, also known as the tip or horn. As will be described in more detail below, some of the parameters that effect droplet size, and consequently particle size, include variables such as the sonication frequency, sonication amplitude, solution viscosity, concentration of the microsphere or particle forming agent, and the flow rate of the particle forming solution coming into contact with the sonication tip. By using preselected combinations of these factors, microparticles are obtainable in the range of less than one micrometer to over 200 micrometers with a relative standard deviation of less than 30%. This is to be contrasted with prior art methods for forming microspheres which are associated with relative standard deviations of higher than 100%.

The inventive methods described herein are also distinguishable from producing a spray from a sonication device by pumping a solution through the sonication device. In the spray technique, the solution is subject to the sonication energy repeatedly, resulting in the formation of smaller particles with a high variability in particle size. However, with the methods of the present invention, the particle forming solution comes in contact with the sonication tip only once without the aid of any pressure beyond atmospheric. This results in a more controlled and uniform production of a stream of particles from the tip of the sonication device.

DETAILED DESCRIPTION OF THE INVENTION

Figure 1:
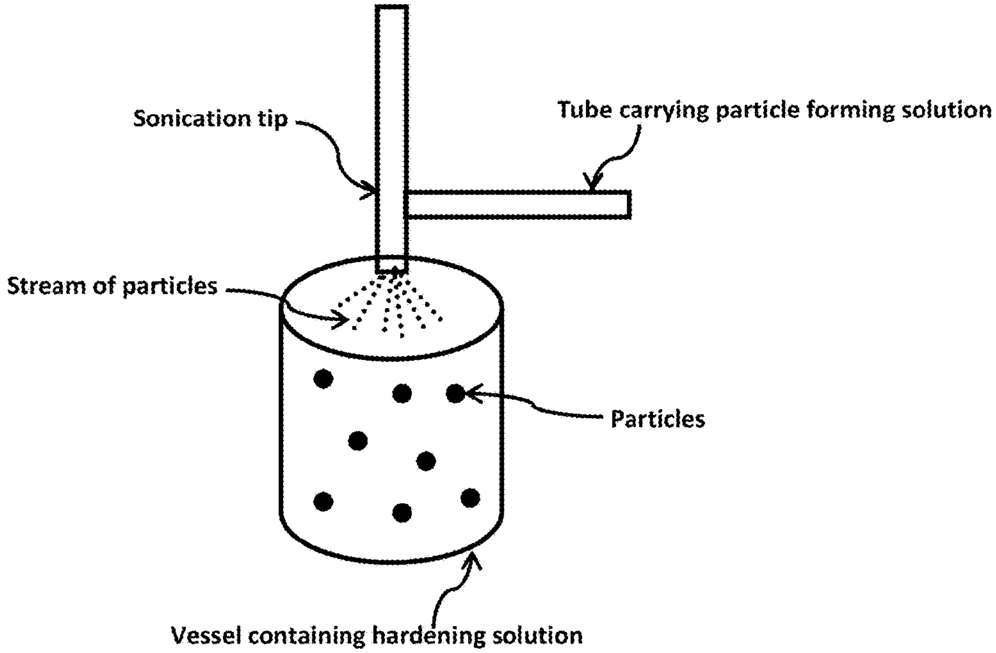
FIG. 1 shows schematic of a process in accordance with the invention showing an apparatus at the point of formation of the particle spray.

With reference to FIG. 1 for purposes of illustration, some preferred aspects of the invention are described. The methods described herein are easily scalable for preparing spherical microspheres of a desired size range by allowing a stream of particle forming solution to come in contact with the tip of a sonication device resulting in formation of a spray of droplets which are preferably transformed into microspheres. The contacting of the sonicating tip with the stream containing the particle forming solution is very brief and is to be contrasted with other microsphere forming techniques using sonication devices in which the sonicating tip is immersed in the particle forming solution for extended periods of time.

After the droplets containing the particle forming solution, which in turn contains the particle forming agent and solvent, are formed, they are allowed to come in contact with a hardening solution. This hardening solution which is described below can be in a container to receive the particle forming droplets or can be continuously moved as a stream to receive the droplets. In this alternative aspect of the method, the stream of particle forming solution comes in contact with the tip of the sonication device and the resulting droplets are directed or added to a continuously flowing stream of the hardening solution. The hardening solution containing the droplets is then collected where the process of hardening of particles is continued.

The sonication tip is operably attached to a sonication device as such devices are known in the art. The terminal part of the device, known by several names including a horn, tip or probe, comes in contact with the polymer forming solution. The sonication tip responds to a range of frequencies to exhibit the process of sonication. The tip can be hollow or solid tube made of a metal or non-metal material. The tip is most commonly round in structure although it is possible to have other shapes as well. The diameter of the tip can range from 0.1 mm to larger than 50 mm, a diameter in the range of 0-1 to 25 mm being the most commonly used size range. While many aspects of the invention will be carried out using one tip on the sonication device, multiple tips can be added to a device in order to increase the rate of processing. In a set-up involving multiple tips, each tip will have its own supply of the particle forming agent.

The process of sonication results in a change in the longitudinal dimensions of the tip. The longitudinal movement of the tip is measured by a parameter known as the amplitude. This longitudinal movement of the tip results in the break up the stream of particle forming solution. The tip of the device can be in close proximity, e.g. from about 0.1 to about 1 mm away from or can be in direct contact with a tube carrying the particle forming solution in the form of a stream. The particle forming solution is allowed to flow over the sonication tip as a constant stream of liquid while the sonication frequency is turned on. The stream of droplets formed from the tip of the device are allowed to fall in a vessel containing the hardening solution that is being constantly stirred with a suitable overhead or magnetic stirring device. The droplets harden either due to loss of the solvent or a chemical reaction with the hardening solution and turn into particles. The dimensions of each component of the system can be varied independently without any limitation.

The tip of the sonication device is connected to a component known as the converter. The converter responds to a range of frequencies generated by a generator. An additional component called as the amplifier is added between the generator and the converter. The purpose of the amplifier is to increase the intensity of the frequency waves generated by the generator before they are sent to the converter. The generator is capable of producing frequencies in the range of less than 5 kilohertz to about 50,000 kilohertz. In suitable sonication devices, the range of from about 15,000 to about 25,000 kilohertz is used for carrying out the methods of the present invention. Some aspects of the invention include a preferred frequency range of from about 18,000 to about 22,000 kilohertz.

The amplifier component of the sonication device is varied to control the intensity of the sonication tip and determines the longitudinal distance traveled by the tip in each wave. In some sonication systems using large diameter tips, i.e. about 20 mm, an additional component called as the booster may be added to the amplifier to further increase the intensity. There is an inverse correlation between the tip diameter and the amplitude. This means that as the diameter of the tip is increased, the same amplitude value results in a smaller longitudinal distance of the tip.

The processes of the invention can be varied by selecting specific combinations of frequency, tip diameter and amplitude. As an example, a half-inch diameter tip at 100% amplitude setting has a longitudinal movement of about 120 micrometers. At 50% amplitude setting, this movement will be about 60 micrometers. The droplet size will be dependent, at least in part, on the longitudinal movement of the tip. A correlation between the size of the tip diameter and the size of the droplets produced is made with other process variables, i.e. frequency, flow rates, concentration and viscosity of the particle forming solution, polymer, etc. being held constant.

Some preferred operating conditions for carrying out the inventive process include sonicating of the sonication tip with a combination of providing a frequency of about 5 to about 40,000 kilohertz and an amplitude of about 10 to about 200 micrometers. The amplitude is set according to the parameters of the polymer solutions. These parameters include but are not limited to the polymer molecular weight (which influences the viscosity of the polymer solution), polymer concentration and the flow rate. In one aspect, the sonicating of the sonication tip is achieved with a combination of providing a frequency of about 18,000 to about 22,000 kilohertz and an amplitude of about 20 to about 100 micrometers. While the specific examples provided below illustrate some preferred parameters with respect to the range of sonication frequency, for example, it will be appreciated is to be understood that a person skilled in the art can see that change of frequency will result in a different size of the particles.

An example of a sonication device having a suitable tip for carrying out the methods of the invention is available from Sonics and Materials, Inc., Newtown, Conn.

After the droplets are formed, they are directed to a hardening solution. The hardening solution can be an aqueous solution containing a suitable surfactant or a non-aqueous liquid such as polyvinyl alcohol (PVA), that allows evaporation of the solvent from particle forming solution, resulting in the formation of solid or semi-solid particles. Examples of suitable surfactants include polyvinyl alcohol, polyvinyl pyrrolidone, sodium lauryl sulfate, sodium oleate, polyethylene glycol, alkali salts of fatty acids, non-ionic surfactants, quaternary ammonium based surfactants, etc. The hardening solution may also contain chemical reagents that react with the particle forming agent to form solid particles. Such reagents can be crosslinking agents known to those of ordinary skill, including, without limitation glutaraldehyde, ethylene glycol di(meth)acrylates, methylenebisacrylamides, and divinylbenzene, etc. which are available, for example from commercial sources such as Sigma-Aldrich Chemical, or synthesized using known techniques.

Some suitable hardening solutions comprise aqueous solutions containing one of the following:

a) polyvinyl alcohol in a concentration of 0.25-4% on w/v basis;

b) sodium lauryl sulfate in a concentration of 0.05-4%;

c) polymethacrylic acid in a concentration of 0.05-4%; and d) Tween 20 or Tween 80 in a concentration of 0.05-10%.

The hardening solutions optionally include additional surfactants and pH controlling agents containing phosphate, acetate, or other buffer ingredients.

The hardening solution may also contain ingredients that undergo a physical or chemical reaction with the particle forming agent to produce crosslinked or otherwise derivatized particles. These particles can be recovered either by filtration or centrifugation and be further processed by lyophilization or another method of drying to obtain dry particles.

The process of hardening the particles can take place at ambient temperature and pressure. The process of hardening can also be aided by the application of low pressure, e.g. from about 0.1 to about 1 ATM to the hardening solution in order to speed up the rate of loss of solvent. Another variation to increase the rate of hardening is to increase the temperature of hardening solution from room temperature to from e.g. from about 30 to about 70 degrees Celsius. A combination of low pressure and higher temperature may also be used to speed up the process of hardening.

In one embodiment of the invention, the hardening of the droplets into particles is achieved by removing the solvent by direct evaporation in the air. In this method, the droplets are subjected to either a high flow rate of the air or a partial or full vacuum to facilitate the process of solvent evaporation. This method may also involve the use of heat to increase the rate of evaporation of the solvent. Evaporation of a portion of the solvent from the particle forming solution by air or vacuum, followed by use of a hardening solution may also be employed.

The methods described herein can be used to prepare microparticles containing only the microparticle forming agent or polymer only. These particles can be used as embolism devices for treating conditions such as cancer or certain cosmetic conditions. Alternatively, the microparticles can also contain one or more active ingredients which can be delivered to the body at a slow rate. The rate of release of these ingredients is controlled by the ratio of the ingredient to the polymer and the molecular weight of the polymer. In addition, the particle size of the microparticles also influences the release rate of the active ingredients.

One of the major advantages of this system is its easy scalability to commercial scale production of microspheres. Since this system produces thousands of particles simultaneously from a single tip and can handle a high flow rate of the solution of the particle forming ingredient, it can be scaled up easily by adding several tips to a system. Additionally, the size of the tip can be increased to handle even higher rates of solution flow to further increase the rate of particle production.

In some aspects of the invention, the microspheres prepared with methods described herein are suitable for encapsulation of a variety of active pharmaceutically acceptable ingredients or medicaments of virtually any therapeutic type, diagnostic agents, dyes, or similar therapeutic or diagnostic agent known to those of ordinary skill. Suitable medicaments can be of highly variable water solubility. As the examples cited below illustrate, the invention described here is capable of producing microspheres containing active ingredients in the water solubility range of 0.0005 mg/L to 500 g/L. Some examples of medicaments are androgenic steroids, anti-allergy agents, anti-infectives, lysozymes, antibiotics, antigens, vaccines, hypnotics, sedatives, interleukins, miotics, steroidal anti-inflammatory agents, non-steroidal anti-inflammatory agents, tranquilizers, cardiovascular agents, sympathomimetics, analgesics, antiparkinsons agents, anti-hypersensitive agents, beta adrenergic blocking agents, nutritional agents, calcitonin, Biguanides, thiazolidinediones, Sulfonylureas, nonsulfonylurea secretagogues, alpha-glucosidase inhibitors, peptide analogs, anti-cholinergics, antihistamines, growth hormones, including human growth hormone, lutenizing hormones, therapeutic proteins and peptides, anticancer agents including alkylating agents, methotrexate, purine antagonists, pyrimidine antagonists, paclitaxel, docetaxel, doxorubicin and daunorubicin, dactinomycin, idarubincin, plicamycin, amsacrine hydroxyurea, asparaginase mitoxantrone, retinoic acid derivatives, bone marrow growth factors, tamoxifen, gonadotropin-releasing hormone agonists, antiarrhythmic agents, amylin agonist analogues, SGLT-2 inhibitors, collagen, antiasthematics, antihistamines, antitussives, bronchodilators, adrenergic bronchodilators, anticholinergic bronchodilators, methylxanthines, decongestants, expectorants, lung surfactants, miscellaneous respiratory agents, respiratory inhalant products, inhaled anti-infectives, inhaled corticosteroids, mast cell stabilizers, mucolytics, upper respiratory combinations, anticoagulants, biologics or antibodies, or fragments thereof or even cosmetics, etc. It will be understood that the foregoing list of therapeutics is provided for purposes of illustrative example rather than a closed list. The only limitations for the active ingredient included in the microspheres is that they be capable of undergoing the sonication process without complete loss of biological activity and be capable of being release from the microspheres in vivo and have a medicinal effect for at least a brief measurable time.

In many aspects of the invention the methods described herein use polylactic co-glycolic acid (PLGA) which is a biodegradable polymer as the particle forming agent. However, the process can also be used to prepare particles from any particle forming polymer or non-polymeric material. Some examples of such materials are: polylactones, polyorthocarbonate, polyhydroxybutyrate, polyalkylcyanoacrylates, polyanhydrides, polyorthoesters, polyester, polyamide, polyglycolides (PGA), and co-polymers of gylcolides such as Polylactic glycolic acid (PLGA), glycolide/lactide polymers (PLLA/PGA), polyorthoester, polyacetates, polystyrene, polycarbonates, polysaccharides, polycaprolactone, L-polylactides, block co-polymers of polyesters and linear or star-polyethyleneglycol, poly-beta-hydroxybutyrate, beta-hydroxyvalerate-copolymers, polyaminoacids, hydrophobized hyaluronic acid, dextrans, starches, methyl methacrylate, acrylamide, bisacrylamide, albumin, cellulose, cellulose-based polymers, chitosan, collagen, gelatin, proteins, Polyvinyl alcohol (PVA), polyvinylpyrrolidone, polyvinylpyridine, and ethylene glycol polymers.

The polymers suitable for this method can be made up of a single monomer or more than one monomer in structure. Molecular weights for the polymer can vary somewhat due to the specific polymer and the commercially available molecular weights. It is contemplated that all such commercially available polymers with molecular weight ranges of from a few thousand to 100,000 or higher with be suitable for use in the methods described herein. An example of a preferred polymer of a single monomer is poly-lactic acid. An example of a polymer with more than one monomer is poly-lactic-glycolic acid. Examples of other polymers include chitosan, polyamides, and many other polymers commonly used in pharmaceuticals, cosmetics and medical devices. The polymers can be biodegradable or may be non-biodegradable in nature. Examples of biodegradable polymers are poly-lactic and poly-lactic-glycolic acid polymers. These polymers are biocompatible and biodegradable and can be injected in to the body by a variety of injection techniques. The above mentioned polymers are commercially available in a variety of molecular weight grades. Typical molecular weights for a preferred polymer, PLGA, range from about 5,000 to about 100,000. It is also possible to have higher molecular weights of the polymer. It is contemplated that the methods of the present invention can be carried any of the without undue experimentation regardless of the molecular weights of polymer selected, it being understood that some slight modifications a parameter such as flow rate of particle forming solution, sonication amplitude or the polymer concentration in the particle forming solution may be desirable.

For purposes of the invention description, the term particle forming agent shall be understood to include the ingredient or ingredients used to make the matrix of the microparticles and does not include any active medicament. The term particle forming liquid shall be understood to include a solvent or a mixture of solvents to dissolve or disperse the particle forming agent or agents. The term particle forming solution shall be understood to include a combination of particle forming liquid and the particle forming agent or agents along with optional ingredients, including active ingredients when desired, as well as auxiliary ingredients useful or desirable for inclusion in the final microspheres. The particle forming solutions described herein will have a solids content of from about 0.1 to about 2% solids. The term hardening solutions shall be understood to include the liquid into which the droplets of particle forming solution are dropped. The hardening solution may contain a combination of surfactants, chemical hardening agents or other ingredients such as buffer systems.

In another aspect of the invention the method is used to prepare microspheres from a solution of microparticle forming agent or polymer containing dispersed agents. The dispersed agents can be solid materials containing polymers or active ingredients. The dispersed agents can also be in the form of a solution which has been emulsified in the microparticle—containing solvent to produce an emulsion. The microparticle forming agent along with the dispersed agent can be processed into microparticles using the methods described herein with the stream containing the particle forming solution having dispersed therein an emulsion containing the active or other desired therapeutic ingredient The stream so configured comes into contact with the sonicating tip and the resulting microparticles will be made up of a matrix of the particle-forming agent along with the dispersed agent embedded in the matrix.

The microparticles prepared by this method may be further coated with additional ingredients to form a second or multiple layers on the particle. These layers can be deposited by the process of spray coating or coacervation techniques well known to those of ordinary skill. The additional coatings may include a polymer or an active ingredient or both.

Another advantage of the methods according to the invention is that the method requires no positive pressure of the solution of particle forming agent. The solution can be allowed to flow under the force of gravity or can be pumped using a suitable device such as a syringe pump or a peristaltic pump. The solution may also be pumped with the aid of a positive pressure at the source. However, none of these pumping methods produce a positive pressure in the liquid line at any time because the line ends at the sonication tip and is open to the atmosphere. This arrangement allows for a system that is free of pressure in the lines.

Another aspect of this invention is its ability to handle concentrated solutions of particle forming agents. As outlined in the examples included in this application, solutions as concentrated as 12% solids in a solvent can be used in this method. This is possible because the solution does not need to be forced through an orifice. It can simply be allowed to flow over a sonication tip.

Another aspect of this invention is that it can process high flow rates of the particle forming solution. By increasing the diameter of the sonication tip, it is possible to process a flow rate in excess of 100 ml per minute on a single tip. This aspect reinforces the scalability aspect of this invention.

Yet another aspect of this invention is its ability to process a particle forming liquid containing suspended agents or dissolved agents. The suspended agents can be active medicaments or particle forming agents. This versatility of the process allows incorporation of suspended particles of a variety of sizes, as large as several micrometers. Absence of an orifice in this device greatly expands its applicability to liquids containing suspending agents.

As will be shown in the examples, the size of the particles formed can be varied from less than one micron to several hundred microns by varying parameters such as the sonication frequency, sonication amplitude, solution viscosity, and concentration of the microsphere forming material, temperature of the polymer solution or suspension, and the flow rate of the particle forming solution. This high particle size range is not believed to have been reported with any other method to date. Since the methods described herein do not involve contacting the sonication tip with the hardening solution, the particles or droplets once formed are not subject to further reduction in size. This allows for a tight control on the final size of the particles as well as the ability to produce particles of highly diverse average particle size, ranging in size from about 1 to about 200 micrometers. Variation of the parameters listed above will result in particles of higher or lower sizes as well without undue experimentation.

As shown in the examples, the size of particles obtained by direct sonication of the polymer solution or suspension in a hardening solution results in formation of particles of very small size, ranging from about 0.1 micrometers to about 2 micrometers.

EXAMPLES

The following examples serve to provide further appreciation of the invention but are not meant in any way to restrict the effective scope of the invention.

Example 1: Formation of Particles of Large Size a) Droplet Formation

Five grams of polylactic co-glycolic acid polymer (50:50), average molecular weight of about 30,000 daltons, are dissolved in 45 milliliters of dichloromethane. This solution is added to a syringe and a syringe pump is used to cause the solution to flow through a tube with an internal diameter of 2 millimeter. The other end of the tube is in touch with a 3 mm diameter sonication tip that is attached to a frequency generator and an amplifier. A vessel filled with 1000 milliliters of a hardening solution containing 1% polyvinyl alcohol in water is placed below the sonication tip or device to receive the droplets. The process of particle production is started by switching the sonication device on to produce sonication energy and starting the syringe pump set to deliver the particle forming solution at a rate of 6 milliliters per minute. The amplitude of the device is set and maintained throughout the process at 20% at a fixed frequency of 20,000 kilohertz. The droplets formed from the sonication tip are collected in the vessel containing the hardening solution which is being constantly stirred with an overhead stirrer. This process is continued until all the particle forming solution has been delivered by the syringe pump.

b) Particle Formation

Figure 2:
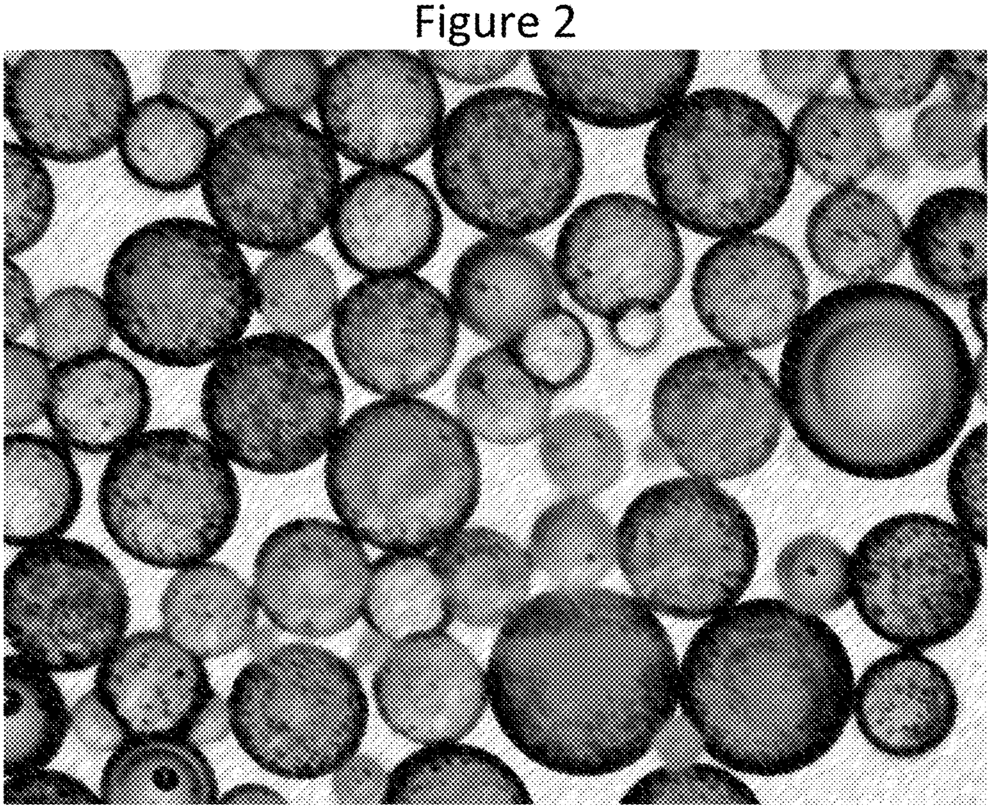
FIGS. 2-3 show microparticles of various sizes formed by Examples 1 and 2, respectively.

The hardening solution containing the droplets of particle forming solution is constantly stirred for a period of 8 hours after which the particles are allowed to settle. The particles are recovered from their suspension by filtration through a filter of less than 5 micrometer pore size. The particles are repeatedly washed with distilled water, re-suspended in a small amount of water and frozen at −40 degree Celsius. The particles are subsequently lyophilized to obtain solid particles. The particle size as measured by microscopy is in the range of 60-200 microns with 80% of the particles being in the range of 90-160 microns, RSD of less than 30%. The particles from this example are shown in FIG. 2.

Example 2: Formation of Particles of Medium Size

Figure 3:
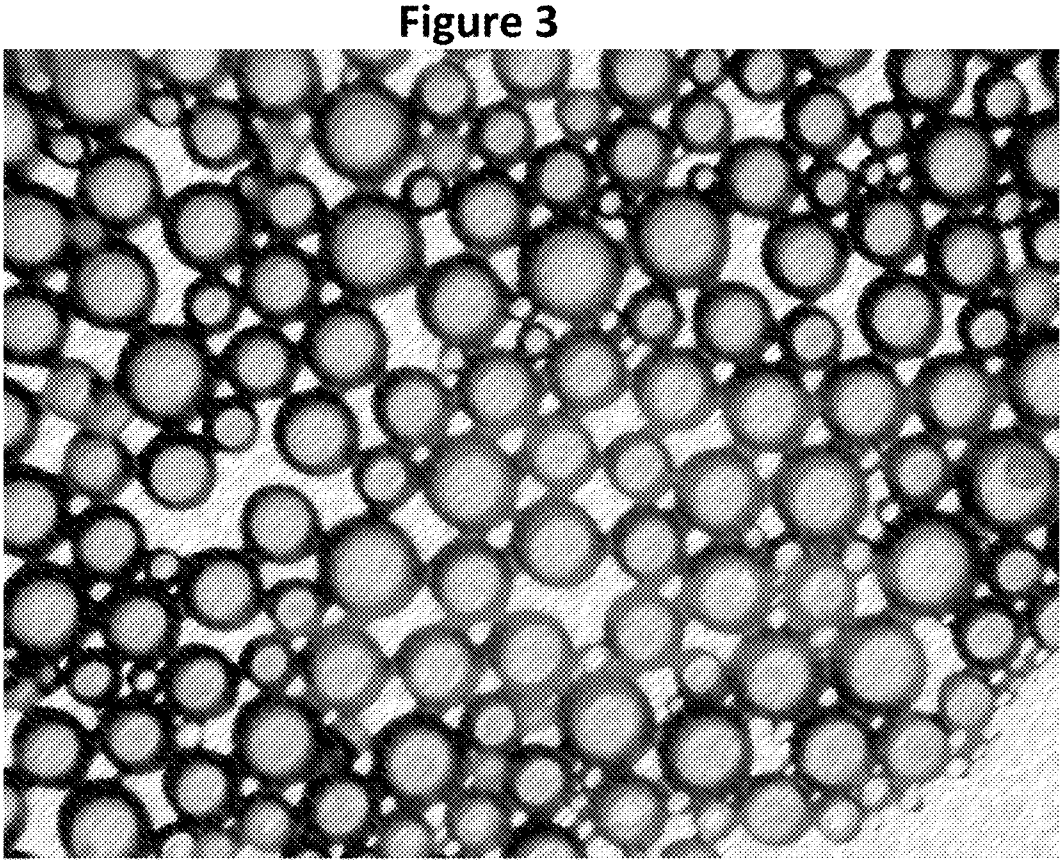

Four grams of polylactic co-glycolic acid polymer (50:50), average molecular weight of about 45,000 daltons, are dissolved in 50 milliliters of dichloromethane. This solution is processed the same way as in Example 1 to prepare microparticles. The particle size as measured by microscopy is in the range of 50-100 microns with 80% of the particles being in the range of 60-80 microns, RSD of less than 30%. The particles from this example are shown in FIG. 3.

Example 3: Formation of Particles from a Primary Emulsion a) Formation of the Emulsion Five grams of polylactic co-glycolic acid polymer (50:50), average molecular weight of about 30,000 daltons, are dissolved in 50 milliliters of dichloromethane. Four milliliters of a phosphate buffer solution of pH 7.4 are added to this solution. The suspension of the buffer in polymer solution is subject to sonication by directly immersing a 3 mm diameter sonication tip operated at 20 kilohertz into the suspension for 2 minutes to produce an emulsion containing small droplets of the buffer in polymer forming solution.

b) Droplet Formation

The emulsion of step a) is added to a syringe and a syringe pump is used to cause the emulsion to flow through a tube with an internal diameter of 2 millimeter. The other end of the tube is in touch with a 3 mm diameter sonication tip that is attached to a frequency generator and an amplifier. A vessel containing 1000 milliliters of 1% polyvinyl alcohol is placed below the sonication tip to receive the droplets. The amplitude of the device is set and maintained throughout the process at 20% at a fixed frequency of 20,000 kilohertz. The process of particle production is started by switching the sonication device on to produce sonication energy and starting the syringe pump set to deliver the particle forming solution at a rate of 6 milliliters per minute.

c) Particle Formation

The droplets formed from the sonication tip are collected in the vessel containing the hardening solution that is being constantly stirred. This process is continued until all the particle forming solution has been delivered by the syringe pump.

The hardening solution containing the droplets of particle forming solution is constantly stirred for a period of 8 hours. The stirring is stopped after 8 hours and the particles are allowed to settle. The particles are recovered from their suspension by filtration through a filter of less than 5 micrometer pore size. The particles are repeatedly washed with distilled water, re-suspended in a small amount of water and frozen at −40 degree Celsius. The particles are subsequently lyophilized to obtain solid particles. The particles are in the size range of 5-30 microns, RSD less than 40%.

Example 4: Particles Containing Testosterone

Two grams of polylactic co-glycolic acid polymer (50:50), average molecular weight of about 18,000 daltons, are dissolved in 50 milliliters of ethyl acetate. 100 milligrams of testosterone as active medicament is added to this solution followed by stirring to obtain a clear solution. This solution is added to a sealed bottle fitted to an air pump to create positive pressure in the bottle. The positive pressure in the bottle causes the solution to flow through a tube with an internal diameter of 2 millimeter. The other end of the tube is in touch with a 3 mm diameter sonication tip that is attached to a frequency generator and an amplifier. A vessel containing 1000 milliliters of 1% polyvinyl alcohol is placed below the sonication tip to receive the droplets. The amplitude of the device is set and maintained throughout the process at 20% at a fixed frequency of 20,000 kilohertz. The process of particle production is started by switching the sonication device on to produce sonication energy and 30 starting the pressure in the vessel to deliver the particle forming solution at a rate of 2 milliliters per minute. The droplets formed from the sonication tip are collected in the vessel containing the hardening solution which is being constantly stirred. This process is continued until all the particle forming solution has been delivered by the syringe pump.

The hardening solution containing the droplets of particle forming solution is constantly stirred for a period of 8 hours, after which the particles are allowed to settle. The particles are recovered from their suspension by subjecting the suspension to centrifugation to obtain a pallet of particles. The particles are repeatedly washed with distilled water followed by centrifugation, re-suspended in a small amount of water and frozen at −40 degree Celsius. The particles are subsequently lyophilized to obtain solid particles. The size of these particles range from 3-20 micrometers, RSD less than 40%.

Example 5: Release Profile

Figure 4:
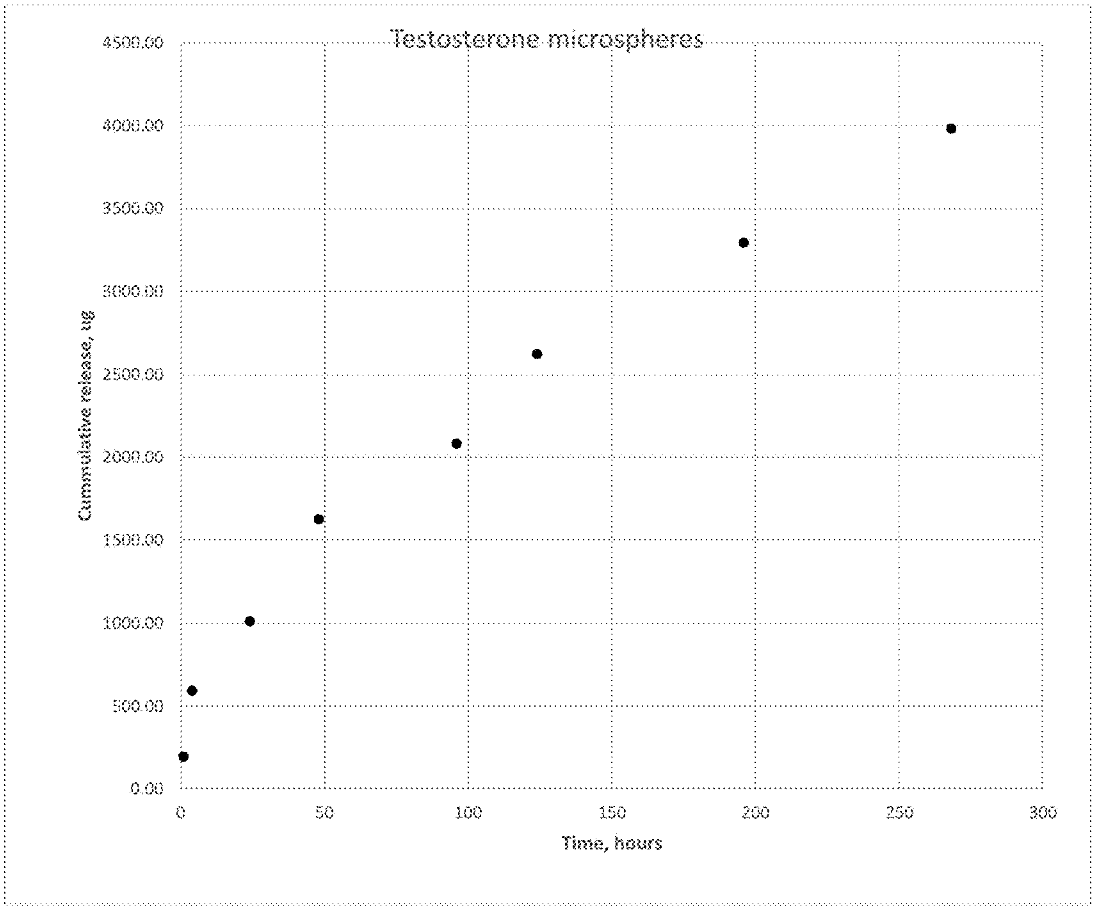
FIG. 4 shows release profile of testosterone, as an example of microspheres containing an active ingredient from polymer particles made in Example 4.

An in vitro release profile for the particles prepared in Example 4 was conducted. One hundred milligrams of the particles from Example 4 were suspended in 5 milliliters of a phosphate buffer of pH 7.4 and added to a dialysis membrane bag with a pore size of molecular weight cut off of 12000. This membrane does not allow the passage of the polymer or the particles but allows the free passage of testosterone. This bag was immersed in 30 milliliters of the same buffer contained in a capped bottle and incubated at 37 degrees Celsius with gentle stirring. Samples of the buffer solution outside of the bag were drawn at predetermined time points, followed by replacement of the 30 milliliters of the buffer with fresh buffer. The content of testosterone released in the buffer was determined by a UV spectroscopic method by comparing with the response to a known concentration of testosterone. The cumulative amount of testosterone release over the entire duration of release was calculated and plotted again time as shown in FIG. 4. As the figure shows, testosterone release over a period of about 11 days linear with time. This release profile, known as the zero-order profile, is an ideal profile for delivery of many active medicaments.

Example 6: Particles Containing Human Serum Albumin

Two hundred and fifty milligrams of polylactic co-glycolic acid polymer (50:50), average molecular weight of about 18,000 dollops, are dissolved in 5 milliliters of dichloromethane. 25 milligrams of purified human serum albumin as an example of active medicament dissolved in 200 microliters of water is added to this solution followed by vortexing for 1 minute to disperse the aqueous solution in dichloromethane solution. This suspension is subject to sonication by dipping a 3 mm sonication tip in the suspension and sonicating at 50% amplitude for 1 minute to form the primary emulsion. This primary emulsion is attached to a syringe pump in a 10 mL syringe which is connected to a tube with an internal diameter of 2 millimeter. The other end of the tube is in touch with a 3 mm diameter sonication tip that is attached to a frequency generator and an amplifier. A vessel containing 100 milliliters of 1% polyvinyl alcohol is placed below the sonication tip to receive the droplets. The amplitude of the device is set and maintained throughout the process at 20% at a fixed frequency of 20,000 kilohertz. The process of particle production is started by switching the sonication device on to produce sonication energy and starting the syringe pump set to deliver the particle forming solution at a rate of 2 milliliters per minute. The droplets formed from the sonication tip are collected in the vessel containing the hardening solution which is being constantly stirred. This process is continued until all the particle forming solution has been delivered by the syringe pump.

The hardening solution containing the droplets of particle forming solution is constantly stirred for a period of 8 hours, after which the particles are allowed to settle. The particles are recovered from their suspension by subjecting the suspension to centrifugation to obtain a pallet of particles. The particles are repeatedly washed with distilled water followed by centrifugation, re-suspended in a small amount of water and frozen at −40 degree Celsius. The particles are subsequently lyophilized to obtain solid particles. The size of these particles range from 5-20 micrometers, RSD less than 40%

Example 7: Formation of Particles of Small Size Range

Two grams of polylactic co-glycolic acid polymer (50:50), average molecular weight of about 7,000 daltons, are dissolved in 50 milliliters of ethyl acetate. This solution is added to a sealed bottle fitted to an air pump to create positive pressure in the bottle. The positive pressure in the bottle causes the solution to flow through a tube with an internal diameter of 2 millimeter. The other end of the tube is in touch with a 3 mm diameter sonication tip that is attached to a frequency generator and an amplifier. A vessel containing 1000 milliliters of 1% polyvinyl alcohol is placed below the sonication tip to receive the droplets. The amplitude of the device is set and maintained throughout the process at 40% at a fixed frequency of 20,000 kilohertz. The process of particle production is started by switching the sonication device on to produce sonication energy and starting the pressure in the vessel to deliver the particle forming solution at a rate of 2 milliliters per minute. The droplets formed from the sonication tip are collected in the vessel containing the hardening solution which is being constantly stirred. This process is continued until all the particle forming solution has been delivered by the syringe pump.

Example 8: CONTROL—Direct Sonication of Solution to Produce Very Small Particles One gram of polylactic co-glycolic acid polymer (50:50), average molecular weight of about 18,000 daltons, is dissolved in 10 milliliters of dichloromethane. This solution is added to 40 milliliters of a 4% solution of polyvinyl alcohol followed by vortexing. A sonication tip of 3 mm diameters is dipped in this solution to a depth of 1 centimeter. The vortexed suspension is sonicated by turning the sonication device on at 20% amplitude and a frequency of 20,000 kilohertz for 1 minute. The resulting emulsion is poured in 100 mL of 1% polyvinyl alcohol solution (hardening solution) with constant stirring. The hardening solution containing the droplets of particle forming solution is constantly stirred for a period of 8 hours after which the particles are recovered by subjecting the suspension to centrifugation to obtain a pallet of particles. The particles are repeatedly washed with distilled water followed by centrifugation, re-suspended in a small amount of water and frozen at −40 degree Celsius. The particles are subsequently lyophilized to obtain solid particles. The size of these particles range from 0.1-2 micrometers. This amounts to a 20-fold difference in particle size range and is not a suitable method when larger particles are desired.

Examples 9-24

Additional examples of microparticles were made following the process of Example 1. The process conditions and resultant particle size of the resultant microparticles are also provided in the Table below.

| Example | PLGA Conc. (% w/v) | Flow rate (ml/min) | Tip Diameter (mm) | Amplitude (%) | Average particle size (microns) | RSD* |
|---|---|---|---|---|---|---|
| 9 | 10 | 20 | 3 | 20 | 105 | 13 |
| 10 | 11 | 20 | 3 | 20 | 116 | 13 |
| 11 | 10 | 20 | 6 | 50 | 101 | 16 |
| 12 | 10.5 | 20 | 3 | 20 | 121 | 17 |
| 13 | 10 | 15 | 6 | 50 | 121 | 20 |
| 14 | 10 | 5 | 6 | 50 | 163 | 20 |
| 15 | 10 | 5 | 6 | 40 | 147 | 21 |
| 16 | 10 | 20 | 6 | 50 | 83 | 21 |
| 17 | 10 | 20 | 6 | 50 | 70 | 23 |
| 18 | 10 | 20 | 3 | 20 | 104 | 23 |
| 19 | 11 | 20 | 3 | 20 | 133 | 25 |
| 20 | 10 | 20 | 3 | 20 | 129 | 26 |
| 21 | 10 | 30 | 6 | 50 | 119 | 27 |
| 22 | 10 | 30 | 6 | 50 | 109 | 28 |
| 23 | 10 | 20 | 6 | 40 | 114 | 29 |

*RSD—relative standard deviation

Examples 24-29

The processes of Examples 1-4 and 6 are repeated except that the polymer is changed from PLGA to ethyl cellulose, viscosity grade about 50. The resulting microparticles are less than about 100 microns in each example.

Examples 30-34

The processes of Examples 1-4 and 6 are repeated except that the hardening solution is changed from 1% polyvinyl alcohol, to a 0.6% sodium laurel sulfate solution. The resulting microparticles are less than about 100 microns in each example.

Examples 35-39

The processes of Examples 1-4 and 6 are repeated except that the hardening solution is changed from 1% polyvinyl alcohol, to a 2.0% Tween 80 solution. The resulting microparticles are less than about 100 microns in each example.

The invention claimed is:

1. A method of preparing a plurality of droplets having a substantially uniform particle size, comprising:

directing a particle forming solution comprising a particle forming liquid and a particle forming agent, as a stream into contact with and over a non-hollow sonicating tip of a sonication device under conditions sufficient to transform the stream containing the particle forming solution into a plurality of droplets having a substantially uniform size;

and contacting the plurality of droplets having a substantially uniform size with a hardening solution under conditions sufficient to solidify the plurality of droplets into a plurality of particles having a substantially uniform particle size.

2. The method of claim 1, further comprising separating the plurality of particles having a substantially uniform particle size from the hardening solution.

3. The method of claim 1, wherein the particle forming liquid includes a solvent selected from the group consisting of dichloromethane, ethyl acetate, acetone, or a mixture thereof.

4. The method of claim 3, wherein the solvent is dichloromethane.

5. The method of claim 1, wherein the particle forming agent is a biodegradable polymer or a non-biodegradable polymer.

6. The method of claim 5, wherein the biodegradable polymer is polylactic co-glycolic acid or polylactic acid.

7. The method of claim 6, wherein the biodegradable polymer is polylactic co-glycolic acid (PLGA), having a molecular weight of from about 7000 to about 100,000.

8. The method of claim 1, wherein the particle forming agent is selected from the group consisting of polylactic acid (PLA), polylactic co-glycolic, acid (PLGA), polyglycolic acid (PGA) polylactones, polyorthocarbonate, polyhydroxybutyrate, polyalkylcyanoacrylates, polyanhydrides, polyorthoesters, polyester, polyamide, polyglycolides (PGA), polyorthoester, polyacetates, polystyrene, polycarbonates, polysaccharides, polycaprolactone, L-polylactides, block co-polymers of polyesters and linear or star-polyethyleneglycol, poly-beta-hydroxybutyrate, beta-hydroxyvalerate-copolymers, polyaminoacids, hydrophobized hyaluronic acid, dextrans, starches, methyl methacrylate, acrylamide, bisacrylamide, albumin, cellulose, cellulose-based polymers, chitosan, collagen, gelatin, proteins, Polyvinyl alcohol (PVA), polyvinylpyrrolidone, polyvinylpyridine, and ethylene glycol polymers.

9. The method of claim 1 wherein the particle forming agent is dissolved in the particle forming liquid.

10. The method of claim 1 wherein the particle forming agent is suspended in the particle forming liquid.

11. The method of claim 1, wherein the particle forming solution further comprises an active ingredient dissolved, suspended or emulsified therein.

12. The method of claim 11, wherein the active ingredient is selected from the group consisting of active therapeutic ingredients having water solubility of from about 0.0005 mg/L to about 500 g/L.

13. The method of claim 1 wherein the concentration of particle forming agent in the particle forming solution is from about 0.1 to about 20 percent, calculated on a weight by volume basis.

14. The method of claim 13, wherein the concentration of particle forming agent in the particle forming solution is from about 0.5 to about 8 percent, calculated on a weight by volume basis.

15. The method of claim 14, wherein the concentration of particle forming agent in the particle forming solution is from about 1.0 to about 6 percent, calculated on a weight by volume basis.

16. The method of claim 1 wherein the concentration of particle forming liquid in the particle forming solution is from about 80 to about 99.9 percent, calculated on a weight by volume basis.

17. The method of claim 16, wherein the concentration of particle forming liquid in the particle forming solution is from about 99.5 to about 92 percent, calculated on a weight by volume basis.

18. The method of claim 17, wherein the concentration of particle forming liquid in the particle forming solution is from about 99 to about 94 percent, calculated on a weight by volume basis.

19. The method of claim 1, wherein the tip of the sonication device has a diameter of from about 0.1 to about 50 millimeters.

20. The method of claim 19, wherein the tip of the sonication device has a diameter of from about 0.5 to about 20 millimeters.

21. The method of claim 19, wherein the tip of the sonication device has a diameter of from about 1 to about 12 millimeters.

22. The method of claim 1, wherein the tip of the sonication device has diameter of greater than about 50 millimeters.

23. The method of claim 1, wherein the particle forming solution contacts the sonicating sonication tip at a rate of from about 0.1 to about 50 milliliters per minute.

24. The method of claim 23, wherein the particle forming solution contacts the sonicating sonication tip at a rate of from about 0.1 to about 1 milliliter per minute.

25. The method of claim 1, wherein the particle forming solution contacts the sonicating sonication tip at a rate of greater than 50 milliliters per minute.

26. The method of claim 1 wherein the stream containing the particle forming solution is directed into contact with the sonicating tip of the sonication device with a tube having an internal diameter of from about 0.1 to about 5 millimeters.

27. The method of claim 1 wherein the stream containing the particle forming solution is directed into contact with the sonicating tip of the sonication device with a tube having an internal diameter of greater than about 5 millimeters.

28. The method of claim 1, wherein the hardening solution comprises an aqueous solution containing a surfactant.

29. The method of claim 28, wherein the surfactant is selected from the group consisting of polyvinyl alcohol, polyvinyl pyrrolidone, sodium lauryl sulfate, sodium oleate, polyethylene glycol, alkali salts of fatty acids, non-ionic surfactants, and quaternary ammonium based surfactants.

30. The method of claim 28, wherein the hardening solution comprises an aqueous solution containing a member of the group consisting of:

a) polyvinyl alcohol in a concentration of 0.25-4% on w/v basis;

b) sodium lauryl sulfate in a concentration of 0.05-4%;

c) polymethacrylic acid in a concentration of 0.05-4%;

d) Tween 20 or Tween 80 in a concentration of 0.05-10%; and said hardening solution optionally includes additional surfactants, and pH controlling agents containing phosphate, acetate, or other buffer ingredients.

31. The method of claim 1, wherein the diameter of the particles is from about 0.1 to about 5 micrometers.

32. The method of claim 1, wherein the diameter of the particles is from about 5 to about 200 micrometers.

33. The method of claim 1, wherein the diameter of the particles is greater than about 200 micrometers.

* * * * *